US00PP34412P2

(12) United States Plant Patent
Gomez Bullis

(10) Patent No.: US PP34,412 P2
(45) Date of Patent: Jul. 5, 2022

(54) ***AECHMEA* PLANT NAMED 'DON JUAN'**

(50) Latin Name: ***(Aechmea eurycorymbus* x *A. aquilegia)* X *(Aechmea blanchetiana* x *A. callichroma)***
Varietal Denomination: 'Don Juan'

(71) Applicant: BULLIS BROMELIADS INC., Princeton, FL (US)

(72) Inventor: Patricia E. Gomez Bullis, Princeton, FL (US)

(73) Assignee: BULLIS BROMELIADS INC., Princeton, FL (US)

( * ) Notice: Subject to any disclaimer, the term of this patent is extended or adjusted under 35 U.S.C. 154(b) by 0 days.

(21) Appl. No.: 17/542,888

(22) Filed: Dec. 6, 2021

(51) Int. Cl.
*A01H 5/02* (2018.01)
*A01H 6/22* (2018.01)

(52) U.S. Cl.
USPC ..... Plt./370
CPC ..... *A01H 6/22* (2018.05); *A01H 6/223* (2018.05)

(58) Field of Classification Search
USPC ..... Plt./370
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Aechmea* plant named 'Don Juan', characterized by its relatively large plant habit with upright growth habit; long and broad green-colored leaves that are variably and heavily tinged with burgundy; freely-flowering habit with large inflorescences held upright and above the foliar plane on straight strong dark red-colored scapes; large upwardly-branched inflorescences with flower bracts that are initially yellow and becoming yellow and dark red with subsequent development; long-lasting inflorescences and good container and interiorscape performance; and relative resistance to Helminthosporium Leaf Spot (*Exserohelium* sp.).

2 Drawing Sheets

Figure 1:
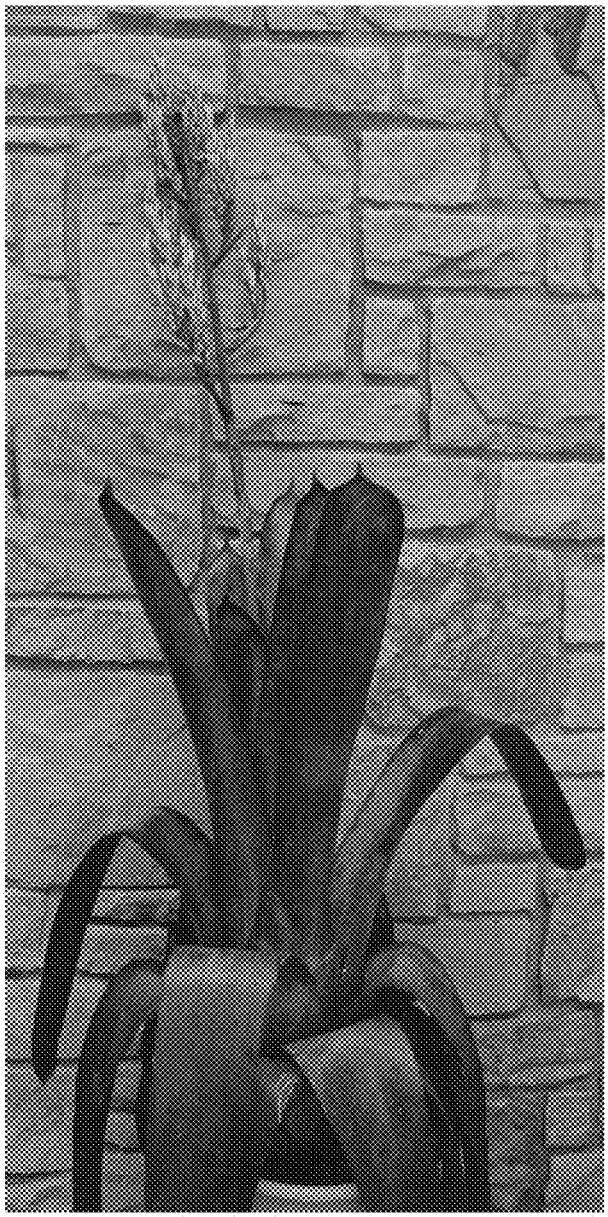

Botanical designation: (*Aechmea eurycorymbus* x *A. aquilegia*) X (*Aechmea blanchetiana* x *A. callichroma*).
Cultivar denomination: 'DON JUAN'.

BACKGROUND OF THE INVENTION

The present invention relates to a new and distinct *Aechmea* plant, botanically known as (*Aechmea eurycorymbus* x *A. aquilegia*) X (*Aechmea blanchetiana* x *A. callichroma*) and hereinafter referred to by the cultivar name 'Don Juan'.

The new *Aechmea* plant is a product of a planned breeding program conducted by the Inventor in Princeton, Fla. The objective of the breeding program was to create new *Aechmea* plants with unique foliage and inflorescence coloration and good postproduction longevity.

The new *Aechmea* plant originated from a cross-pollination made by the Inventor in June, 2011 in Princeton, Fla., of an unnamed selection of *Aechmea eurycorymbus* X *A. aquilegia*, not patented, as the female, or seed, parent with an unnamed selection of *Aechmea blanchetiana* X *A. callichroma*, not patented, as the male, or pollen, parent. The new *Aechmea* plant was discovered and selected by the Inventor as a single flowering plant from within the progeny of the stated cross-pollination in a controlled greenhouse environment in Princeton, Fla. in August, 2012.

Asexual reproduction of the new *Aechmea* plant by offsets in a controlled greenhouse environment in Princeton, Fla. since January, 2013 has shown that the unique features of this new *Aechmea* plant are stable and reproduced true to type in successive generations.

SUMMARY OF THE INVENTION

Plants of the new *Aechmea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Don Juan'. These characteristics in combination distinguish 'Don Juan' as a new and distinct *Aechmea* plant:

1. Relatively large plant habit with upright growth habit.
2. Long and broad green-colored leaves that are variably and heavily tinged with burgundy.
3. Freely-flowering habit with large inflorescences held upright and above the foliar plane on straight strong dark red-colored scapes.
4. Large upwardly-branched inflorescences with flower bracts that are initially yellow and becoming yellow and dark red with subsequent development.
5. Long-lasting inflorescences and good container and interiorscape performance.
6. Relatively resistant to Helminthosporium Leaf Spot (*Exserohelium* sp.).

Plants of the new *Aechmea* differ from plants of the female parent selection primarily in the following characteristics:

1. Plants of the new *Aechmea* have green-colored leaves that are variably and heavily tinged with burgundy whereas plants of the female parent selection have green-colored leaves blushed with red.
2. Plants of the new *Aechmea* have broader leaves than plants of the female parent selection.
3. Inflorescences of plants of the new *Aechmea* are upwardly branching and yellow to yellow and red in color whereas inflorescences of plants of the female parent selection are mostly horizontally branching and reddish in color.

4. Plants of the new *Aechmea* are more resistant to Helminthosporium Leaf Spot (*Exserohelium* sp.) than plants of the female parent selection.

Plants of the new *Aechmea* differ from plants of the male parent selection primarily in the following characteristics:

1. Leaves of plants of the new *Aechmea* are darker in color than leaves of plants of the male parent selection.
2. Plants of the new *Aechmea* have broader leaves than plants of the male parent selection.
3. Inflorescences of plants of the new *Aechmea* are upwardly branching whereas inflorescences of plants of the male parent selection are upwardly and horizontally branching.

Plants of the new *Aechmea* can be compared to plants of *Aechmea blanchetiana* 'Pinot Noir', not patented. In side-by-side comparisons, plants of the new *Aechmea* and 'Pinot Noir' differ primarily in the following characteristics:

1. Leaves of plants of the new *Aechmea* are darker in color than leaves of plants of 'Pinot Noir'.
2. Plants of the new *Aechmea* have broader leaves than plants of 'Pinot Noir'.
3. Inflorescences of plants of the new *Aechmea* are upwardly branching whereas inflorescences of plants of 'Pinot Noir' are mostly horizontally branching.

BRIEF DESCRIPTION OF THE PHOTOGRAPHS

The accompanying colored photographs illustrate the overall appearance of the new *Aechmea* plant showing the colors as true as it is reasonably possible to obtain in colored reproductions of this type. Colors in the photographs may differ slightly from the color values cited in the detailed botanical description which accurately describe the colors of the new *Aechmea* plant.

The photograph on the first sheet (FIG. 1) is a side perspective view of a typical flowering plant of 'Don Juan' grown in a container.

Figure 2:
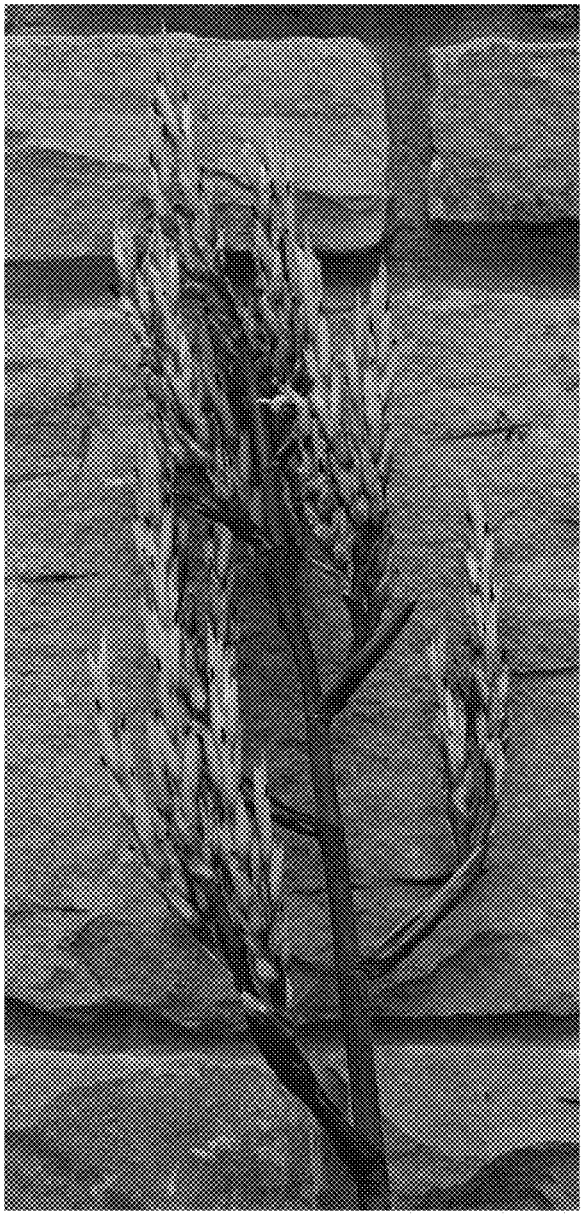

The photograph on the second sheet (FIG. 2) is a close-up view of a typical inflorescence of a plant of 'Don Juan'.

DETAILED BOTANICAL DESCRIPTION

The aforementioned photographs and following observations, measurements and values describe plants grown in 25-cm containers during the spring and summer in a polypropylene-covered shadehouse in Princeton, Fla. During the production of the plants, day temperatures ranged from 19° C. to 35° C., night temperatures ranged from 19° C. to 30° C. and light levels ranged from 4,000 to 5,500 foot-candles. Plants were one year from planting when the photographs and description were taken. In the following description, color references are made to The Royal Horticultural Society Colour Chart, 2015 Edition, except where general terms of ordinary dictionary significance are used.

Botanical classification: (*Aechmea eurycorymbus* x *A. aquilegia*) X (*Aechmea blanchetiana* x *A. callichroma*) 'Don Juan'.

Parentage:

*Female, or seed, parent*.—Unnamed selection of *Aechmea eurycorymbus* X *A. aquilegia*, not patented.

*Male, or pollen, parent*.—Unnamed selection of *Aechmea blanchetiana* X *A. callichroma*, not patented.

Propagation:

*Type*.—By vegetative offsets.

*Time to initiate roots, summer*.—About 30 to 45 days at temperatures ranging from 30° C. to 35° C.

*Time to initiate roots, winter*.—About 45 to 60 days at temperatures ranging from 19° C. to 24° C.

*Time to produce a rooted young plant, summer*.—About three months at temperatures ranging from 30° C. to 35° C.

*Time to produce a rooted young plant, winter*.—About five months at temperatures ranging from 19° C. to 24° C.

*Root description*.—Medium in thickness, fibrous; typically light brown in color, actual color of the roots is dependent on substrate composition, water quality, fertilizer type and formulation, substrate temperature and physiological age of roots.

Rooting habit: Moderately freely branching; medium density.

Plant description:

*Plant and growth habit*.—Upright growth habit; rosette leaves are erect when young, becoming slightly outwardly to downwardly arching with subsequent development; plants readily produce offsets; vigorous growth habit.

*Plant height, soil surface to top of leaf canopy*.—About 87 cm.

*Plant height, soil surface to top of inflorescence*.—About 143 cm.

*Plant diameter or spread*.—About 62 cm.

Leaf description:

*Arrangement*.—Rosette, spiral phyllotaxis; leaves clasping; simple.

*Length*.—About 74 cm.

*Width, flattened*.—Distally, about 10 cm; at the base, about 16 cm.

*Shape*.—Lanceolate, strap-like.

*Apex*.—Sharply cuspidate to aristate.

*Base*.—Truncate.

*Margin*.—Pectinate; sharply spinose.

*Aspect*.—Initially, upright and becoming outwardly to downwardly arching with subsequent development.

*Texture and luster, upper and lower surfaces*.—Smooth, glabrous; leathery; stiff; moderately glossy to glossy.

*Venation*.—Parallel.

*Color*.—Developing and fully expanded leaves, upper surface: Close to 146A variably and heavily overlain with close to 187A; towards the margins, close to 187A; venation, similar to lamina color. Developing and fully expanded leaves, lower surface: Close to 146A to 146B variably and heavily overlain with close to 187A; towards the margins, close to 187A; venation, similar to lamina color.

*Marginal spines*.—Density: About four per cm. Length: About 2 mm. Diameter, proximally: About 1.5 mm. Shape: Acicular with sharp apices. Texture and luster: Smooth, glabrous; glossy. Color: Close to 187A.

Inflorescence description:

*Inflorescence form and arrangement*.—Long, open terminal panicles with upwardly branched lateral panicles supported by erect and strong scapes; about eight to eleven primary lateral panicles each with about four to six secondary lateral panicles each with about 15 to 18 individual flowers; flowers distichous and sessile.

*Inflorescence longevity*.—Inflorescences of the new *Aechmea* are very long-lasting, typically bract color will be maintained for about two to three months in the greenhouse and about two to five months in the interior landscape depending on environmental conditions; flowers and inflorescences persistent.

*Fragrance*.—None detected.

*Inflorescence length*.—About 54.5 cm.

*Inflorescence width*.—About 19.5 cm.

*Primary lateral panicle length*.—About 20 cm.

*Primary lateral panicle width*.—About 6 cm to 9 cm.

*Secondary lateral panicle length*.—About 13.5 cm.

*Secondary lateral panicle width*.—About 2.5 cm.

*Flower length*.—About 2.75 cm.

*Flower diameter*.—About 7.5 mm.

*Petals*.—Quantity and arrangement: Three in a single whorl; fused at least 90% of the length. Length: About 2.25 cm. Width, proximally: About 5 mm. Shape: Elongated ovate to lanceolate. Apex: Acute. Base: Truncate. Margin: Fused; at apex, entire. Texture and luster, inner and outer surfaces: Smooth, glabrous, waxy; glossy. Color: When opening and fully opened, inner surface: Close to 157A. When opening and fully opened, outer surface: Proximally, close to 157A; distally, close to 158A and at the edges, close to 60A.

*Sepals*.—To date, sepal development has not been observed on plants of the new *Aechmea*.

*Primary or scape bracts*.—Quantity and arrangement: One subtending each lateral panicle. Length: About 12 cm. Width, flattened: About 2.75 cm. Shape: Lanceolate. Apex: Acuminate. Base: Truncate. Margin: Entire. Texture and luster, upper and lower surfaces: Smooth, glabrous; moderately glossy. Color, upper surface: Close to 59A to 59B. Color, lower surface: Close to 59A.

*Flower bracts*.—Quantity and arrangement: One per flower; subtending and closely appressed to the flower. Length: About 2.75 cm. Width, flattened: About 1 cm. Shape: Broadly ovate. Apex: Acute. Base: Truncate. Margin: Entire. Texture and luster, upper and lower surfaces: Smooth, glabrous, waxy; glossy. Color, outer surface: Close to 7A; with subsequent development, proximally, close to 53A and towards the apex and margins, close to 7A; at the apex, close to 187A. Color, inner surface: Close to between 7A and 9A; with subsequent development, proximally, close to 58A and towards the apex and margins, close to between 7A and 9A.

*Scapes*.—Length, primary, to base of lowermost panicle: About 75 cm. Diameter, primary: About 1.4 cm. Length, laterals: About 5.1 cm. Diameter, laterals: About 6 mm. Strength, primary and laterals: Strong. Aspect, primary: Upright. Aspect, laterals: Curving upwardly. Texture and luster, primary and laterals: Smooth, glabrous; densely covered with trichomes; slightly glossy. Color, primary and laterals: Close to 53A.

*Reproductive organs*.—Stamens: Quantity per flower: Six. Filament length: About 4 mm. Filament color: Close to 162A to 162B. Anther length: Less than 1 mm. Anther shape: Oblong. Anther color: Close to 162C. Pollen: None observed.

*Pistils*.—Quantity per flower: One. Pistil length: About 2.4 cm. Style length: About 1.6 cm. Style color: Close to 163C. Stigma shape: Ovoid. Stigma color: Close to N163D. Ovary color: Close to 157A.

*Seeds*.—To date, seed production has not been observed on plants of the new *Aechmea*.

Temperature tolerance: Plants of the new *Aechmea* have been observed to tolerate temperatures ranging from about 3° C. to about 37° C.

Pathogen & pest resistance: Plants of the new *Aechmea* have been observed to exhibit relative resistance to Helminthosporium Leaf Spot (*Exserohelium* sp.). Plants of the new *Aechmea* not been observed to be resistant to pests and other pathogens common to *Aechmea* plants.

It is claimed:

1. A new and distinct *Aechmea* plant named 'Don Juan' as illustrated and described.

* * * * *